United States Patent
Arnone

(10) Patent No.: US 10,966,812 B2
(45) Date of Patent: Apr. 6, 2021

(54) EMBOLIC PROTECTION SYSTEM

(71) Applicant: Epic Medical Concepts & Innovations, INc., Olathe, KS (US)

(72) Inventor: Joshua Clay Arnone, Wentzville, MO (US)

(73) Assignee: Epic Medical Concepts & Innovations, Inc., Olathe, KS (US)

(*) Notice: Subject to any disclaimer, the term of this patent is extended or adjusted under 35 U.S.C. 154(b) by 132 days.

(21) Appl. No.: 16/177,158

(22) Filed: Oct. 31, 2018

(65) Prior Publication Data

US 2019/0125514 A1     May 2, 2019

Related U.S. Application Data

(60) Provisional application No. 62/579,448, filed on Oct. 31, 2017.

(51) Int. Cl.
*A61F 2/01*       (2006.01)

(52) U.S. Cl.
CPC ............. *A61F 2/013* (2013.01); *A61F 2/01* (2013.01); *A61F 2/011* (2020.05); *A61F 2002/016* (2013.01); *A61F 2002/018* (2013.01); *A61F 2230/001* (2013.01); *A61F 2230/0067* (2013.01); *A61F 2230/0069* (2013.01)

(58) Field of Classification Search
CPC .... A61F 2/01; A61F 2/013; A61F 2/86; A61F 2/88; A61F 2/885
See application file for complete search history.

(56) References Cited

U.S. PATENT DOCUMENTS

| | | | |
|---|---|---|---|
| 7,052,511 B2* | 5/2006 | Weldon | A61F 2/95 623/1.11 |
| 2011/0190662 A1* | 8/2011 | McWeeney | A61B 17/1114 600/567 |
| 2012/0041538 A1* | 2/2012 | White | A61F 2/90 623/1.12 |
| 2014/0330305 A1 | 7/2014 | Rood et al. | |
| 2015/0112377 A1 | 4/2015 | Arnone et al. | |

* cited by examiner

*Primary Examiner* — Tuan V Nguyen
(74) *Attorney, Agent, or Firm* — Erickson Kernell IP, LLC; Aaron S. Reed

(57) ABSTRACT

An embolic protection and filtration device (EFD) that is deployable within the aortic arch of a patient to prevent emboli from entering the coronary arteries. The device includes a collapsible tubular chassis having enlarged opposing end portions and a midsection of smaller radial dimension. A filtration membrane is disposed at least on upstream and midsection portions of the chassis and is configured to filter and shunt large emboli down the descending aorta and away from the coronary arteries. A retrieval device is provided for retrieving the EFD from within the patient. The retrieval device automatically compensates for elongation of the EFD as the EFD is radially contracted such that the EFD is not moved or drug along the aorta as it is collapsed and retracted into a retrieval catheter.

15 Claims, 6 Drawing Sheets

EMBOLIC PROTECTION SYSTEM

CROSS-REFERENCE TO RELATED APPLICATIONS

This application claims the benefit of U.S. Provisional Patent Application No. 62/579,448 filed Oct. 31, 2017 the disclosure of which is hereby incorporated herein in its entirety by reference.

BACKGROUND

One of the largest unmet needs in transcatheter aortic valve replacement (TAVR) procedures is stroke prevention. As the mechanical valve is deployed—either by balloon catheter or by a self-expanding valve structure—it crushes the old stenotic valve, releasing a shower of debris known as emboli into the blood stream. These embolic particles are subsequently swept into the nearby arteries that supply blood to the brain, often leading to stroke and death.

Studies have shown that "the 30-day incidence of major or disabling stroke is 3.4% to 8%, and most of these events occur within the first 24 to 48 hours after TAVR." Diffusion-weighted MRI scans have also revealed that the occurrence of "silent" embolisms—those that present no immediate side effects but have unknown long-term effects—is anywhere from 50% to 80% of patients. Although the frequency and/or severity of these events may be mitigated by improved surgical procedures, there is general consensus that no procedural efforts can eliminate the threat of stroke.

One of the newest directions in TAVR valve development is the ability to manipulate and reposition the valve to secure a tighter seal and better performance. Although this represents a significant potential improvement for long-term health outcomes, this repositioning also represents the potential unleashing of even more emboli, further emphasizing the need for an embolic protection system.

These risks limit expansion of TAVR to all aortic valve replacement patients and are a driver for embolic protection accessories. Clinicians need a device to use in conjunction with a valve that is able to provide effective and reliable cerebral protection in an easy to use platform without introducing additional risk or morbidity.

Previous Design Iteration

To meet the clinical need described above an embolic filtration device (EFD) has been developed that, when deployed within the aortic arch, deflects emboli down the descending aorta to prevent neurological dysfunctions such as stroke. This EFD is described in detail in U.S. Patent Application Publication Nos. 2014/0330305 to Rood et al. filed Jul. 3, 2014 and 2015/0112377 to Arnone et al. filed Nov. 7, 2014 the disclosures of each of which are hereby incorporated herein in their entirety by reference. One embodiment of such device is depicted in FIG. 1 and referred to generally as the EFD 10.

As described in the '305 and '377 publications, the known EFD 10 consists of a shape-memory nitinol stent supporting an elastic, biologically compatible filtration membrane and a retrieval system. The stent is characterized as a braided, self-expanding tube with a generally bi-conical configuration in which the cross-sectional area of the device varies with respect to length so that, when fully expanded, only segments of the device near the ends thereof are in contact with the aorta. This configuration reduces the risk of further embolic formation, reduces tissue irritation at the cerebral vessel junctions, and lessens the potential for the device and additional catheters to mechanically dislodge emboli from vessel walls. The stent structure is configured to provide a stiffness that is sufficiently rigid to maintain its shape and stability while implanted while also not posing a risk of arterial rupture from stent spring-back. The stent diameter within the mid-section is large enough for additional catheter passage during surgery, but small enough to avoid direct contact with the aorta.

The filtration membrane of the known EFD 10 extends along the mid-section of the EFD 10. The membrane may be fabricated by laser-drilling a polycarbonate urethane membrane that may be bonded directly to the stent. The filtration membrane is configured to maximize mechanical integrity while allowing it to be drilled with holes that will not significantly deform or tear. Laser drilling of the membrane provides 100-micron pore size that has negligible effect on blood flow to the brain, yet deflects potential stroke-causing emboli down the descending aorta without harmful consequences (the general consensus is emboli less than 100 microns in size have minimal or no potential for causing stroke).

As further described by the '305 and '377 publications, the bi-conical shape of the EFD 10 provides outwardly flaring end portions joined together by the mid-section which comprises an elongate cylindrical form. The conical, outwardly flaring ends are at least partially covered or coated with a non-porous membrane or jacket that encloses the end portion and directs fluid flow toward and through the mid-section. This configuration of the end portions may transmit hemodynamic forces in the radial direction, which may aid to further anchor the device in place without relying solely on the radial force provided by expansion of the stent.

As further described in the '305 and '377 publications, this known EFD 10 is introduced into the aortic arch via trans-femoral catheterization at the beginning of the procedure, and remains completely detached from the outside environment for the operation's duration. Once placed in the desired position, the EFD 10 can remain completely detached from any outside anchoring device (i.e. the delivery catheter). This not only frees up the "work space"—within the aorta as well as the on the operating table—but also allows for short-term implantation following a TAVR procedure. The EFD 10 may remain implanted for several hours following surgery in order to continue filtering debris away from the patient's brain, which will eliminate virtually all of the post-operative strokes currently faced by this procedure.

Removal is then made possible through the use of the magnetic retrieval system. This feature entails a "drawstring" that is looped though the distal end of the stent with a small neodymium magnet connected to the end. When deployed in the aorta, the magnet dangles in the wake of the device—within the descending aorta downstream from the stent. Once the TAVR procedure is complete and at the point that embolic protection is no longer necessary, a retrieval catheter is used to remove the device from the patient.

A corresponding magnet at the tip of a retrieval-catheter makes the initial attachment to the EFD 10, even under limited or no fluoroscopic visibility. A mechanical latching mechanism may then be used to fully secure the magnetic connection. Slightly pulling back on the catheter by the surgeon pulls the drawstring and causes the drawstring to substantially completely close the diameter of the stent at the distal end. A slider on the catheter handle can then be advanced to retract the drawstring into the catheter while the surgeon advances the catheter toward and over the entire EFD 10, collapsing it in place. Translation of the EFD 10 within the aorta as it is captured by the retrieval-catheter is preferably limited in order to minimize the potential for tissue damage. Once the EFD 10 is sufficiently enclosed within the retrieval catheter, the catheter is removed from the femoral artery. This removal technique eliminates risks associated with current methods, which involve "fishing" with a hook, which may lead to an increased risk of arterial damage and extended procedure duration.

Although the known EFD 10 devices described by the '305 and '377 publications and depicted in FIG. 1 make great strides toward increasing patient safety in TAVR procedures, several drawbacks remain. In the known EFD 10, the drawstring configuration has a tendency to become entangled with the stent structure and/or with itself. Further, the non-porous jacket or membrane on the ends of the EFD 10 can cause difficulties during deployment when interacting with blood flow through the aorta which can damage the EFD 10 and temporarily impede blood flow to the patient. And the retrieval methods described in the '305 and '377 publications rely on manual movement of the catheter by the surgeon to collapse the EFD 10 and to accommodate elongation of the EFD 10 as it is collapsed. If such movements are not precise, the EFD 10 may be dragged along the interior wall of the aorta which can lead to irritation and/or damage thereto.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes an improved embolic filtration device (EFD) that includes a refined structure for retaining a drawstring that is useable to collapse the EFD, an improved filter membrane configuration, and an improved retrieval catheter that accounts for an increase in length of the stent as the stent is collapsed and drawn into the catheter.

The EFD includes a mesh or braided, collapsible wire stent structure forming an elongate tube with radially outwardly flaring or enlarged end portions joined together by a mid-section of a reduced radial dimension. A porous membrane is provided on the stent structure and extends from an upstream end of the stent structure to a downstream end of the mid-section and/or partially beyond the downstream end of the mid-section. Blood and fluid flow along and around contact areas between the EFD and the aorta is thus enabled to decrease the propensity for emboli formation in these areas.

An upstream edge of the membrane is formed to generally follow an undulating pattern of an upstream edge of the stent. As such, pockets formed by the membrane extending between the undulations of the stent structure are removed. Such pockets might otherwise provide locations in which blood and fluids might be trapped and emboli formed.

A downstream end of the stent is provided with a plurality of fingers formed by elongate loops of the stent wire extending in the downstream direction. Downstream ends of the fingers are provided with eyelets configured to receive a drawstring therethrough. The drawstring is threaded through the eyelets to encircle the circumference of the downstream end of the stent in an expanded state and to provide a tail that dangles downstream from the EFD with a retrieval component at a distal end thereof. The eyelets retain the drawstring in position at distal ends of the fingers and resist entanglement of the drawstring with the stent, with apparatus employed during a medical procedure, and with the drawstring itself, including the tail thereof.

The retrieval catheter employed to retrieve the EFD from its position within the aorta of the patient is configured to accommodate lengthening of the EFD as it is collapsed radially so as to eliminate need for the surgeon to manually adjust the catheter position as the EFD is retrieved. The retrieval catheter includes a handle with an actuatable mechanism that retracts the drawstring into the catheter a first distance while simultaneously advancing a sheath of the catheter a second distance. The first distance is proportional to the second distance in a ratio equal to that of the change in the length of the EFD between the expanded and collapsed state relative to the total length of the EFD in the collapsed state.

DESCRIPTION OF THE DRAWINGS

Illustrative embodiments are described in detail below with reference to the attached drawing figures, and wherein.

DETAILED DESCRIPTION

The subject matter of select exemplary embodiments is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about," "approximately," or "substantially" as used herein denote deviations from the exact value by +/−10%, preferably by +/−5% and/or deviations in the form of changes that are insignificant to the function.

Figure 1:
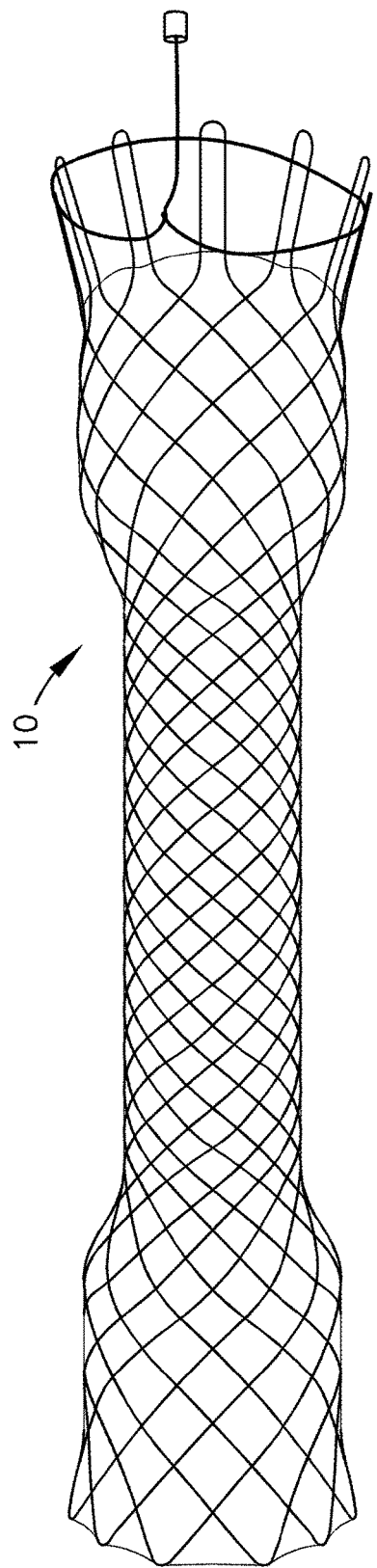
FIG. 1 is side elevational view of a prior art embolic filtration device (EFD) prototype used in bench and porcine tests.
Figure 2:
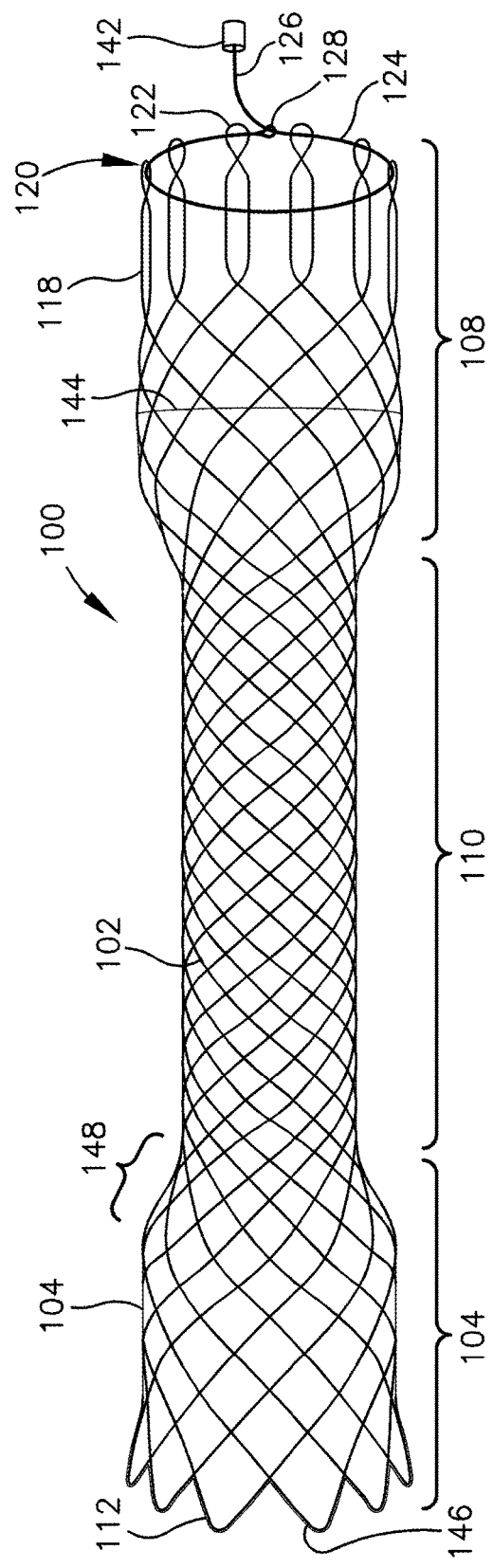
FIG. 2 is a side elevational view of an improved embolic filtration device depicted in accordance with an exemplary embodiment and wherein fingers on a backside of the device are not shown for clarity.
Figure 3:
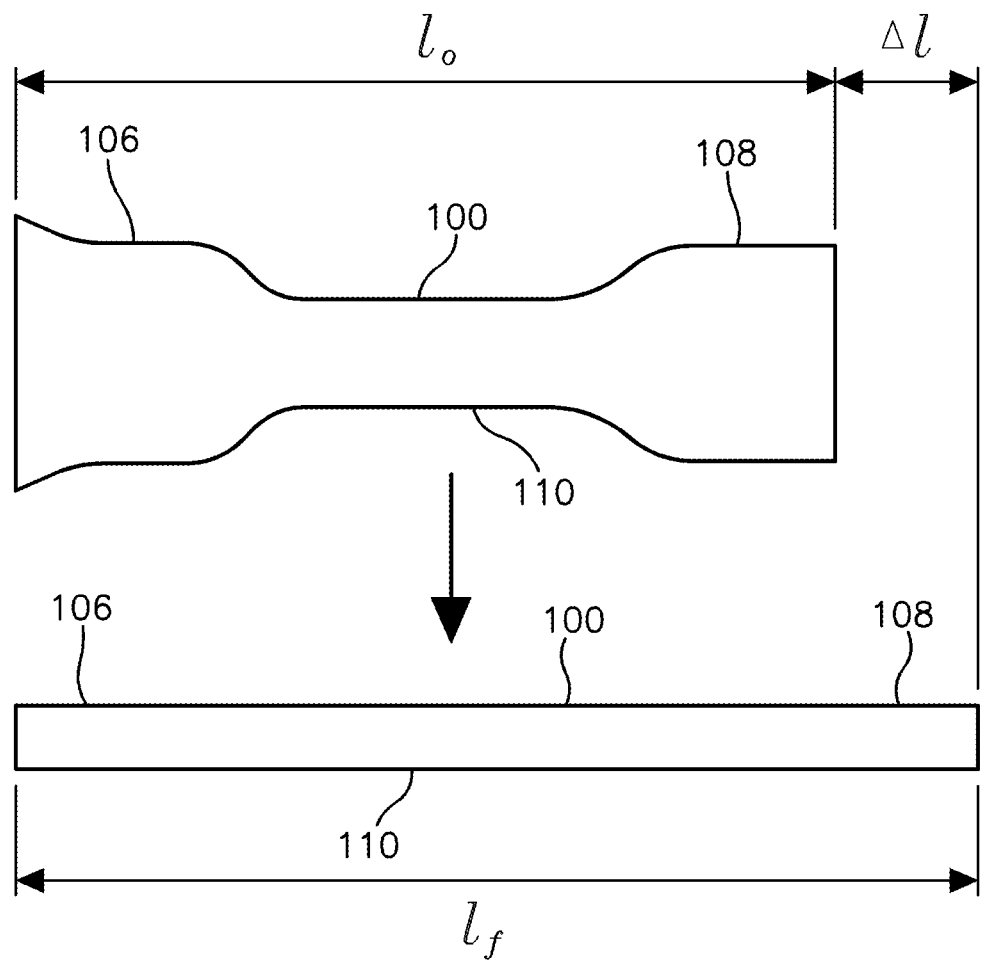
FIG. 3 is a schematic view depicting a change in length of an embolic filtration device between an expanded state and a collapsed state in accordance with an exemplary embodiment.
Figure 4:
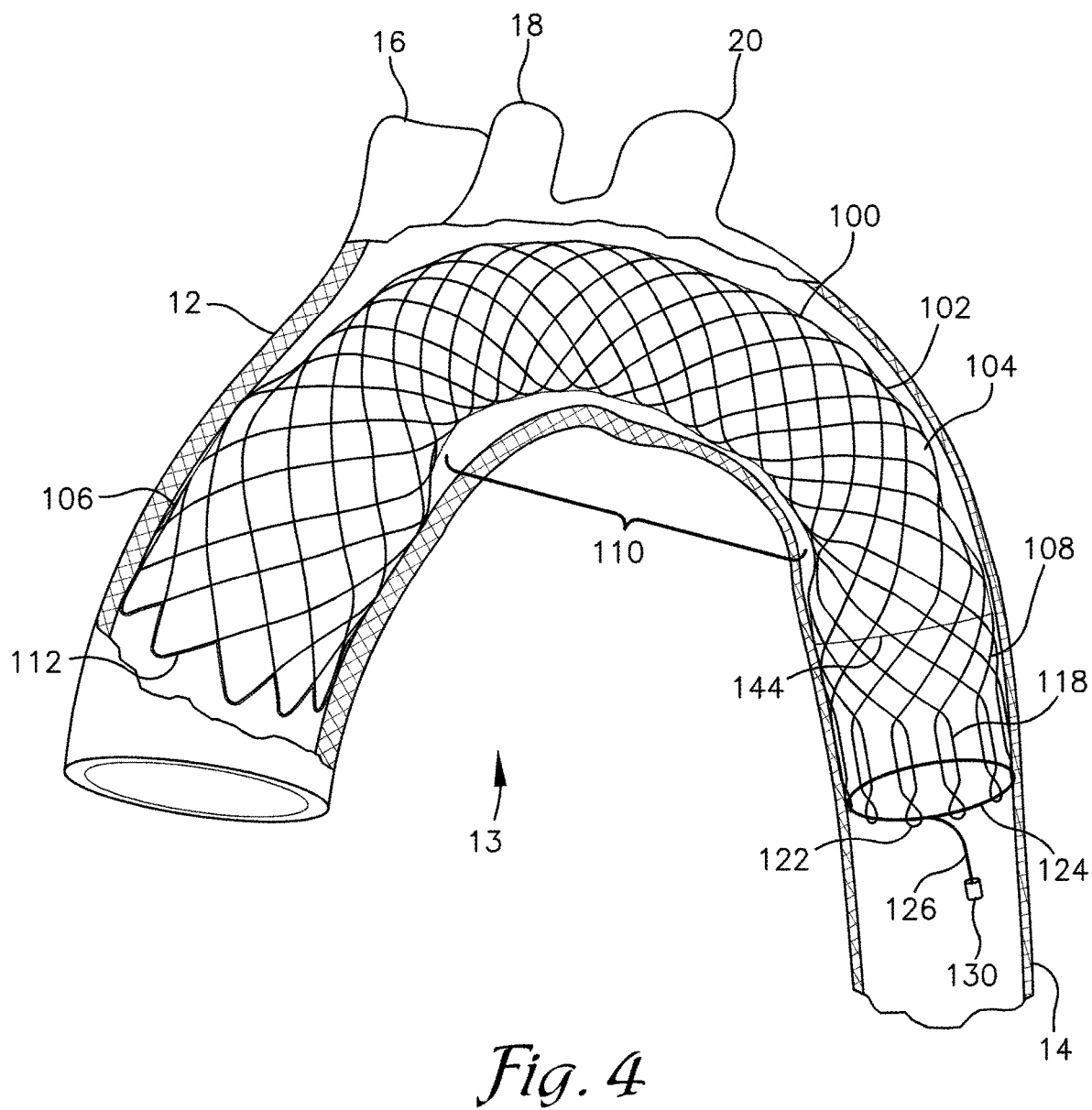
FIG. 4 is a partial cross-sectional view of a human aorta depicting the embolic filtration device of FIG. 2 deployed therein in accordance with an exemplary embodiment.

With reference to FIGS. 2-4, an embolic filtration device (EFD) 100 is described in accordance with an exemplary embodiment. The EFD 100 is configured for placement within an aorta 12, particularly within an aortic arch 13, of a patient during a procedure, such as a TAVR procedure, to direct emboli and/or other debris of a size sufficient to present substantial risk of harm to the patient, down the descending aorta 14 and away from the brachiocephalic 16, carotid 18, and subclavian arteries 20 (also referred to herein as the coronary arteries 16, 18, 20).

Like the EFD device described in the '305 and '377 publications, the EFD 100 comprises a braided wire chassis 102 with a filtration membrane 104 disposed thereon. The '305 and '377 publications, the disclosures of which are incorporated herein by reference, provide additional detail of materials and construction methods that may be employed for EFD devices; reference is made to those publications for such detail. As such, only a limited description of such details is provided herein. Embodiments of the EFD 100 may employ the materials and construction methods described by the '305 and '377 publications among others known in the art without departing from the scope of embodiments described herein.

The chassis 102 is described herein as being formed from one or more braided wires, however it is understood that the chassis 102 may be formed by other means including, for example a laser cut tube, expanded metal, or the like without departing from the scope of embodiments described herein. The chassis 102 can be formed from a metallic wire such as a stainless steel or titanium alloy that may include shape memory properties, but other metallic and non-metallic materials can be employed. In one embodiment, the chassis 102 is comprised of a shape memory nitinol wire.

As depicted in FIG. 3, the chassis 102 is provided with an elongate form that is collapsible from an expanded state (shown in FIG. 2) to a collapsed state that is suitable for disposal within a deployment and/or retrieval catheter. In the expanded state, the chassis 102 forms a hollow tube having enlarged upstream and downstream portions 106, 108 that are joined by a midsection 110 of a reduced diameter relative to that of the upstream portion 106 and the downstream portion 108. The upstream and downstream portions 106, 108 may have the same or different dimensions and may be configured with the same or different form. As depicted in FIG. 2, the upstream portion 106 has slightly larger dimensions than that of the downstream portion 108 and the upstream portion 106 is provided with a bell-shaped form while the downstream portion 108 is substantially cylindrical. However, the upstream and downstream portions 106, 108 may be provided with a variety of varied forms configured to provide a desired engagement and/or contact area with the interior surface or intima of the aorta 12.

The dimensions of the upstream portion 106 are sufficient to contact the interior surface of a patient's aorta 12. The dimensions may be selected and correlated with the material properties of the material from which the chassis 102 is formed to provide a radially outward bias and force that is sufficient to engage the interior surface of the aorta 12 to form a seal therewith and to retain the EFD 100 in position during a procedure but that is also less than a force that might create a substantial risk of rupturing the aorta 12.

The downstream portion 108 is also dimensioned to contact the interior surface of the aorta 12 to provide a seal therebetween and to aid retention of the EFD 100 in place during the procedure. In some embodiments, the force applied to the interior surface of the aorta 12 by the downstream portion 108 is less than that applied by the upstream portion 106.

The downstream portion 108 includes a plurality of fingers 118 spaced about the circumference of a terminal edge 120 of the downstream portion 108 and extending in an axial direction therefrom. The fingers 118 are formed by U-shaped segments of the wire forming the chassis 102 as the wire extends from the chassis 102 and then turns or bends back toward the chassis 102 to re-enter the braided structure thereof. It is understood that the fingers 118 may be formed by other methods and structures in accordance with a particular chosen construction method for the EFD 100.

A distal end of each of the fingers 118 includes an eyelet 122. As depicted in FIG. 2, the eyelet 122 is formed by a twist in the wire forming the finger 122 to form an enclosed opening or loop at the distal end of the finger 118. In another embodiment, the eyelet 122 may be formed by coupling a ring or similar component to the distal end of the finger 122, such as by welding. The eyelets 122 are positioned and configured to receive a drawstring 124 that is threaded through the eyelets 122 about the circumference of the EFD 100. The eyelets 122 are dimensioned to substantially maintain a longitudinal position of the drawstring 124 at the distal ends of the fingers 118 while also enabling sliding movement of the drawstring 124 through the eyelets 122.

The drawstring 124 encircles the open end of the downstream portion 108 and slideably engage itself before extending downstream to form a tail 126. A first end of the drawstring 124 may include a loop 128 through which the opposite second end may be threaded to provide the slideable engagement. In another embodiment, the drawstring 124 may be tied upon itself in a slipknot or lasso-like fashion, among other techniques that allow the tail 126 to be pulled to constrict the open end of the downstream portion 108.

A retrieval component 130 is coupled to the opposite second end of the drawstring 124 at the terminal end of the tail 126. The retrieval component is configured for engagement and capture by a retrieval catheter 132 during removal of the EFD 100 form within the patient's aorta. The retrieval component 130 may also be employed for loading of the EFD 100 in a deployment catheter 152 prior to deployment in the patient's body. The retrieval component 130 should be sized and configured to enable the component 130 to be disposed within both the deployment catheter 150 and a retrieval catheter 132 without interfering with operation of the respective catheter 150, 132.

Figure 5:
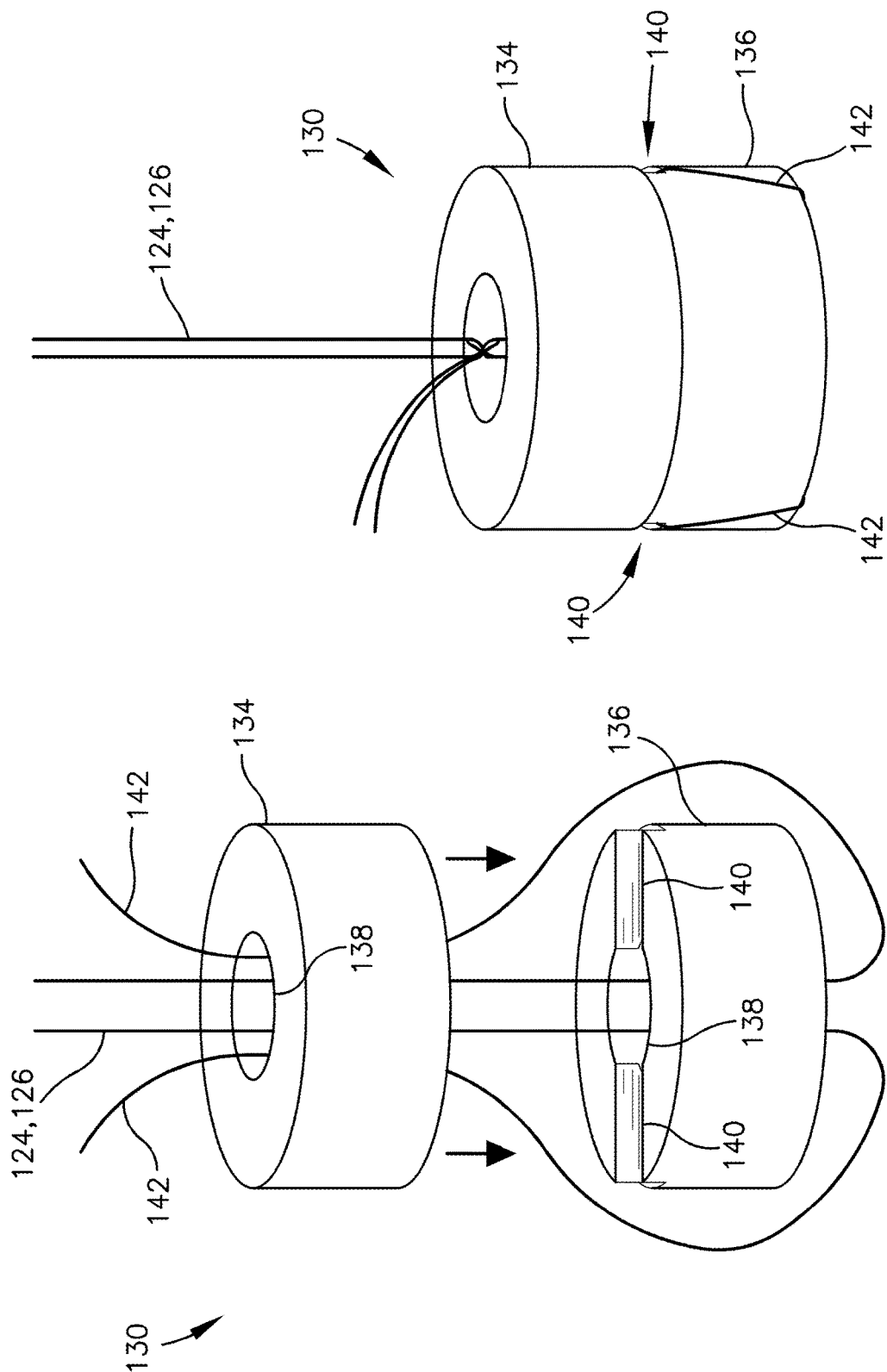
FIG. 5A is a perspective view of a retrieval component comprised of a pair of magnets depicted in an unassembled state in accordance with an exemplary embodiment.
FIG. 5B is a perspective view of the retrieval component of FIG. 5A in an assembled state depicted in accordance with an exemplary embodiment.

As depicted if FIG. 2, the retrieval component 130 preferably comprises a pair of magnets 134, 136, such as neodymium magnets, coupled to the distal end of the tail 126. Such a configuration provides the retrieval component 130 with a compact size while also providing sufficient magnetic attraction for capture and engagement with the retrieval catheter 132 as described more fully below. In one embodiment depicted in FIG. 5 the magnets 134, 136 include a cylindrical form with a central, axial bore 138 extending therethrough. The magnets 134 and 136 are assembled and coupled to the drawstring 124 in a stacked configuration. The bottom magnet 136 in the stack is provided with a pair of diametrical notches 140 in an end face thereof that are configured to receive the drawstring 124 therein such that the end face of the bottom magnet 136 can abut an opposing face of the top magnet 134 with the drawstring captured therebetween and in the notches 140.

The assembly and coupling of the magnets 134, 136 with the drawstring 124 is thus formed by receiving the drawstring 124 through the bores 138 of the magnets 134, 136. At least an end portion of the drawstring 124 is bifurcated to provide a pair of side-by-side members 142. In one embodiment, the drawstring 124 comprises a single member that is doubled over to provide the loop 128 at one end and the side-by-side members 142 throughout the length thereof. In another embodiment, side-by-side members 142 of the drawstring 124 may be braided, encased, wrapped, or otherwise joined along at least a portion of the length of the drawstring 124. The members 142 are directed in opposite directions along a bottom surface of the bottom magnet 136 and around sides of the magnet 136 to engage respective ones of the notches 140. The members 142 are then passed back through the bore 138 of the top magnet 134 and tied or secured in place. The magnets 134, 136 (or the retrieval component 130) may be coated or encased with a biocompatible material, such as silicon or similar material that may aid to reduce irritation of the aorta 12, biologic interaction with the retrieval component 130, and/or to aid mechanical interaction between the retrieval component 130 and the retrieval catheter 132 or the deployment catheter 150.

With continued reference to FIGS. 2 and 4, the midsection 110 of the EFD 100 is a substantially uniform, cylindrical tube extending between the upstream and downstream portions 106, 108. As depicted in FIG. 4, the midsection 110 has sufficient length to extend along the aorta 12 from a position upstream of the brachiocephalic artery 16 to a position downstream of the subclavian artery 20 and has sufficient flexibility to bend and follow an arched form of the aorta 12. The midsection 110 is configured with a diametrical dimension that is smaller than that of the interior of the aorta 12 such that when in the expanded state and deployed in the aorta 12, the midsection preferably does not contact the interior surface of the aorta 12, as depicted in FIG. 4.

The filtration membrane 104 comprises a sheet or thin layer of material that is bonded or coupled to the exterior or interior surface of the chassis 102 to enclose the circumference of the chassis 102 and provide a tube-like form thereto. In one embodiment, the chassis 102 is embedded in the filtration membrane 104 and/or is coated with a membrane material. The membrane 104 extends from the upstream edge 112 of the upstream portion 106 to a downstream end of the midsection 110. The membrane 104 may terminate shortly upstream or downstream of the downstream end of the midsection 110 but should extend beyond or downstream of the subclavian artery 20 when deployed in a patient. In one embodiment, a downstream termination 144 of the membrane 104 extends downstream to a contact point between the downstream portion 106 and the aorta 12 to provide a seal between the downstream portion 108 and the aorta 12, as depicted in FIG. 4. Such a seal may provide an additional safeguard against emboli exiting the downstream end of the midsection 110 and being drawn into the coronary arteries 16, 18, 20.

The filtration membrane 104 is permeable to fluids and particles that are smaller in size than a predetermined maximum dimension. The maximum dimension may be selected based on a particle or emboli dimension that, if passed through the coronary arteries 16, 18, 20 to the brain or other vital organs of the patient, may have a high likelihood of causing a stroke or other harm to the patient. Emboli having a diameter of greater than about 100 microns (μm) are generally considered to be hazardous emboli by those of skill in the art. In one embodiment, the maximum dimension is approximately about 125 μm or about 100 μm or about 75 μm. The filtration membrane 104 may be formed from a polycarbonate urethane material among a variety of other materials that are biologically compatible and that have sufficient elastic properties to enable expansion and collapse of the chassis 12. The membrane material may be perforated such as by laser-drilling among other methods or a porous material may be selected. Perforation of the membrane material preferably provides perforations having the approximate maximum dimension and in sufficient number and configuration to provide a desired flow rate through the membrane 104 to support the biological needs of the patient (i.e. blood flow to the coronary arteries 16,18, 20) while the EFD 100 is deployed in the patient's aortic arch 13.

As depicted in FIG. 2, at the upstream edge 112 of the EFD 100, the membrane 104 is configured to follow shape of the chassis 102. The upstream edge of the chassis 102 is formed by a plurality of U-shaped loops of the wire forming the chassis 102. As such, the upstream edge 112 has an undulating or scalloped form with a plurality of projections 146. The membrane 104 is formed to follow the undulating form of the projections 146 to substantially eliminate portions of the membrane 104 from the space between the projections 146.

Such portions of the membrane 104 between the projections 146 may have a propensity to form pockets between the membrane 104 and the interior surface of the aorta 12 which may enable formation of emboli. Elimination of such pockets thus also eliminates risks of emboli formation therein. Elimination of these additional portions of the membrane 104 also reduces the contact area between the upstream end 106 of the EFD 100 and the aorta 12 which may reduce risks of irritating surfaces of the aorta 12.

Additionally, provision of the membrane 104 with perforations and/or permeability throughout the midsection 110 and the upstream portion 106 of the EFD 100 aids flow of blood and fluids through the membrane 104 along the entire length of the EFD 100. As such, the propensity for formation of emboli between the EFD 100 and the interior surfaces of the aorta 12 is decreased. For example, enabling blood and fluid flow through the membrane 104 in the upstream portion 106 may reduce the occurrence of emboli-forming eddies or stagnant pools that form between the EFD 100 and the aorta 12, especially in areas along a transition zone 148 or necked down portion of the upstream portion 106 between the upstream portion 106 and the midsection 110. Permeability in contact areas between the EFD 100 and the aorta 12 may also reduce irritation of the surfaces of the aorta 12.

Figure 6:
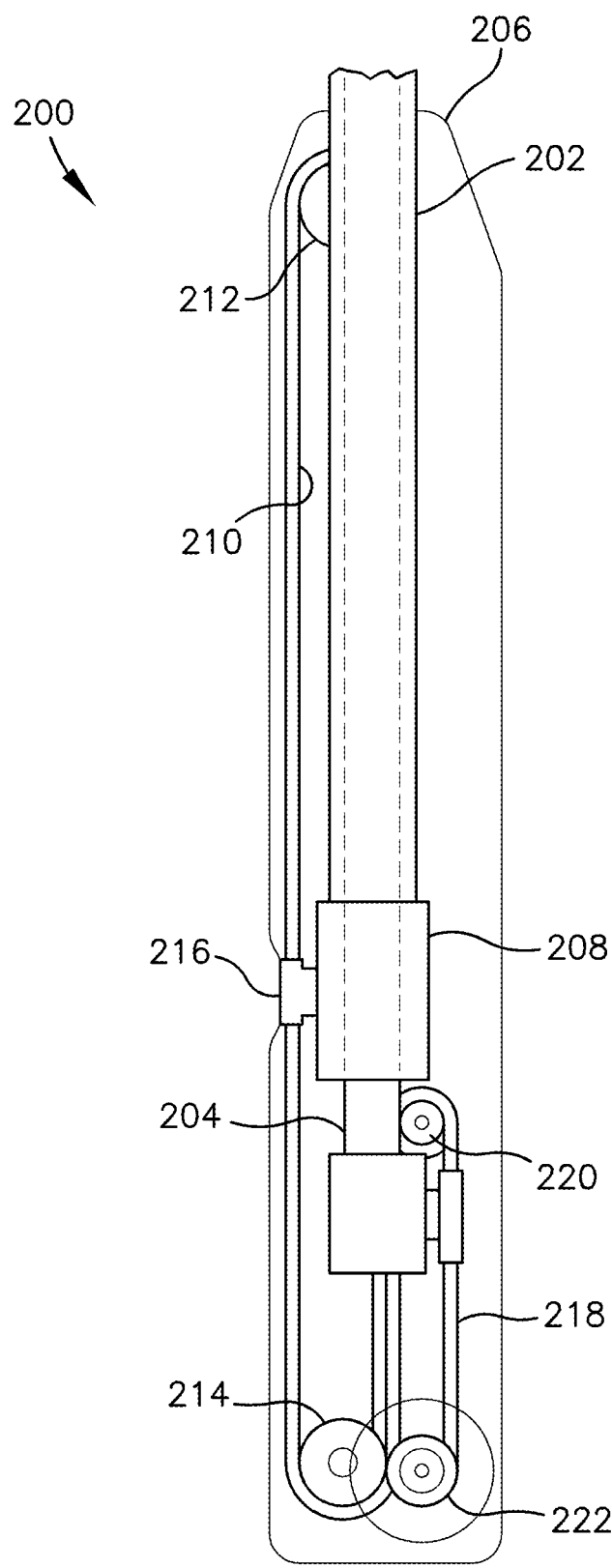
FIG. 6 is a diagram of internal components of a retrieval catheter system for use with the embolic filtration device of FIG. 2 depicted in accordance with an exemplary embodiment.

With reference now to FIG. 6, an EFD retrieval device 200 for use in combination with the retrieval catheter 132 for retrieval of the EFD 100 from within a patient's aorta 12 is described in accordance with an exemplary embodiment. As depicted in FIG. 3, the EFD 100 lengthens axially as it is collapsed from the expanded state to the collapsed state. The retrieval device 200 includes a mechanism for taking into account this elongation of the EFD 100 during radial collapse thereof. In order to collapse the EFD 100 in place within the aorta 12, a sheath 202 of the retrieval catheter 132 is advanced upstream over the EFD 100 while a core 204 of the catheter 132 attached to the retrieval component 130 is retracted downstream. The ratio of core retraction relative to sheath advancement can be described by the equation:

$$\frac{d_c}{-d_s} = r = \frac{\Delta l}{l_f}$$

Where:

$d_c$ is the change in position of the core 204;

$d_s$ is the change in position of the sheath 202;

Δl is the change in length of the EFD 100 between the expanded and collapsed state; and $l_f$ is the total length of the EFD 100 in the collapsed state.

As depicted in FIG. 6, the EFD retrieval apparatus 200 is incorporated within a handle 206 of the retrieval catheter 132 itself such that the catheter handle 206 remains stationary during the process of collapsing the EFD 100. The apparatus 200 includes a slider 208, a sheath cable 210, a sheath pulley 212, and a sheath gear 214. The slider 208 is coupled to the sheath 202 of the retrieval catheter 132 and is slideably moveable longitudinally within the handle 206 to move the sheath 202 longitudinally. At least a portion of the slider 208 is exposed exterior to the handle 206 to provide a contact surface or thumb tab 216 that is engageable by a user to extend/retract the sheath 202.

The sheath pulley 212 and the sheath gear 214 are disposed on opposite longitudinal sides of the slider 208. The sheath cable 210 comprises an elongate cable, wire, band, strap, or the like that is coupled at both ends to the slider 208 and/or to the sheath 202 to form a loop that extends around the sheath pulley 212 and the sheath gear 214. As such, longitudinal, sliding movement of the slider 208 moves the sheath cable 210 around the sheath pulley 212 and the sheath gear 214 and rotates the sheath gear 214.

The apparatus 200 also includes a core cable 218, a core pulley 220, and a core gear 222. The core cable 218 comprises a cable, wire, band, strap, or the like and is coupled to the core 204 of the retrieval catheter 132. The core cable 218 is looped around the core pulley 220 and the core gear 222 which are disposed on opposite longitudinal sides of the coupling point between the core cable 218 and the core 204. As such, longitudinal movement of the core 204 corresponds with rotational movement of the core gear 222.

The sheath gear 214 and the core gear 222 mechanically engage, such as through intermeshing of gear teeth therebetween in a gear ratio equal to r as described in the above equation. Thus, movement of the slider 208 by the surgeon/user a longitudinal distance, $d_s$ in a first longitudinal direction moves the sheath 202 the distance $d_s$ in the first direction and, through the sheath cable 210, rotates the sheath gear 214 in a first rotational direction. The core gear 222 is thereby rotated in an opposite second rotational direction which, through the core cable 218, moves the core 204 a longitudinal distance, $d_c$ in a second longitudinal direction, opposite the first longitudinal direction, wherein $d_c = r*(-d_s)$. These movements are provided with the handle 206 remaining stationary and, at the opposite end of the retrieval catheter 132, translate into advancement of the sheath 202 toward EFD 100 the distance $d_s$ and retraction of the core 204 and the EFD 100 into the sheath 202 the distance $d_c$ in the opposite direction. The sheath 202 is thus advanced toward the EFD 100 and the EFD 100 is radially collapsed and drawn into the sheath 202 without translational movement of the EFD 100 relative to the aorta 12.

In contrast, by known methods and apparatus like those described in the '305 and '377 publications, a surgeon is relied upon to manually withdraw the retrieval catheter to accommodate the lengthening of the EFD as she retracts the EFD into the retrieval catheter. This procedure is undesirable because it requires too much precision from the surgeon to be accomplished to perfection, especially when the surgeon must operate blindly without being able to see the movements of the EFD and retrieval catheter. Imprecision in the surgeon's movements may cause the EFD to be moved or drug along the walls of the aorta 12 which may lead to release of emboli and/or irritation or damage to the aortic intima.

It is understood that one of skill in the art will recognize alternative configurations that may be employed to provide movement of the sheath 202 relative to the core 204 in the desired ratio, r. Such configurations may include linear gears, worm gears, gear trains, electronics, or hydraulic or pneumatic actuators, among others. For example, the sheath cable 210 might be replaced with a toothed band and the sheath gear 214 replaced with a pulley; rotation of the core gear 222 could then be provided by engagement of the toothed band with the core gear 222. Or a configuration employing one or more electric motors adapted to provide movement of the sheath 202 and core 204 at the desired ratio might be employed. Such configurations are within the scope of embodiments described herein.

With continued reference to FIGS. 2-6, deployment and retrieval of the EFD 100 in the aortic arch of a patient is described in accordance with an exemplary embodiment. In some embodiments, a surgeon first installs a guidewire 158 in the patient's femoral artery and extending to a desired position in the aorta 12 to guide subsequent apparatus into position during a surgical procedure as is common in the art.

The EFD 100 is loaded into the deployment catheter 150 by radially collapsing the EFD 100 and drawing it into the interior of a sheath 152 of the deployment catheter 150. The deployment catheter includes the sheath 152 with a core 154 disposed coaxially therein in a manner similar to that described with respect to the retrieval device 200. The core 154 provides an axial passage 156 through which the guidewire 158 is installed. The deployment catheter 150 can thus be slideably guided along the guidewire 158 into position within the patient.

A carriage 160 configured to engage the retrieval component 130 of the EFD 100 may be affixed to the core 154 to aid drawing the EFD 100 into the deployment catheter sheath 152 and maintaining a coupling with the EFD 100 during deployment. In one embodiment, the carriage 160 is configured to partially deflect the core 154 away from axial alignment with the sheath 152 to provide sufficient space for the retrieval component 130 to be housed inside the sheath 152 alongside the core 154. The deflection of the core 154 is minimized such that the sliding movement of the core 154 along the guidewire 158 is not substantially affected.

Figure 7:
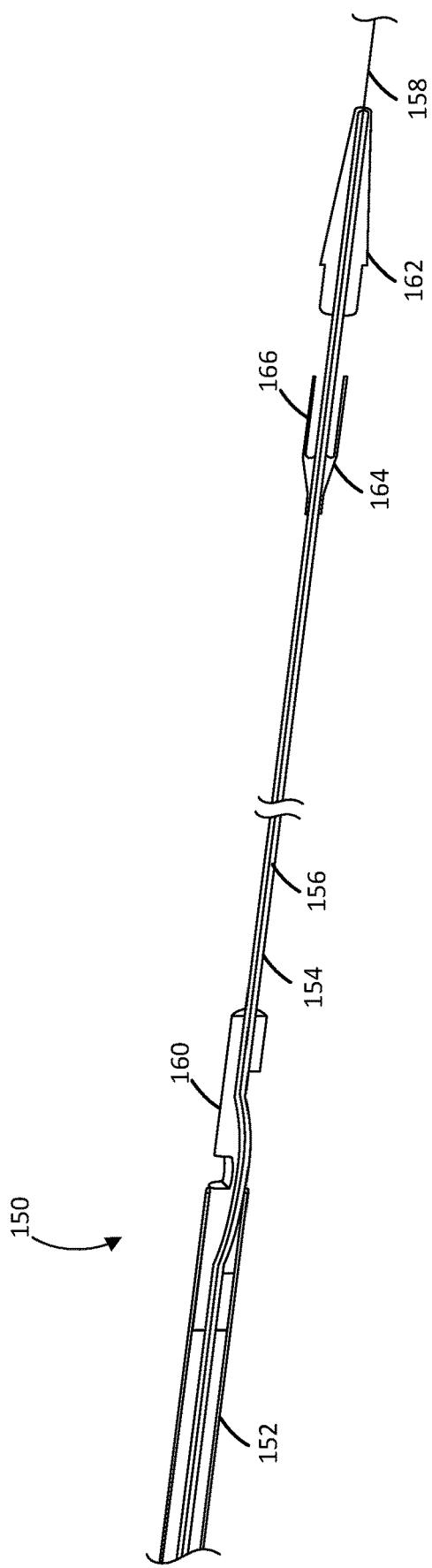
FIG. 7 is a cross-sectional view of a deployment catheter for deployment of the embolic filtration device in a patient depicted in accordance with an exemplary embodiment.

In one embodiment, the core 154 of the deployment catheter 150 includes a conical tip 162 disposed at a distal end thereof. A forked retainer component 164 is disposed on the core 154 near the conical tip 162 and includes a plurality of prongs 166 extending toward the conical tip 162 and spaced radially outwardly from the core 154. The prongs 166 may engage the EFD 100 to aid in extracting the EFD 100 from the catheter sheath 152 during deployment but then release the engagement to allow the EFD 100 to expand to the expanded state. In one embodiment, the prongs 166 maintain engagement with the EFD 100 in the collapsed state until the sheath 152 is retracted beyond the retainer component 130 in the carriage 160 (as depicted in FIG. 7) at which point the retainer component 130 is released and the chassis 102 is allowed to expand the EFD 100 to the expanded state. In another embodiment, release of the engagement between the prongs 166 and the EFD 100 may be accomplished by slightly retracting the core 154.

The deployment catheter 150 is inserted into the patient's femoral artery and guided into the aorta 12 and aortic arch of the patient by known procedures. Upon obtaining proper positioning of the deployment catheter 150, the EFD 100 is discharged from within the catheter 150. In one embodiment, the EFD 100 is retained in the collapsed state until being fully deployed by retaining tension on the drawstring 124. Once tension is released, the chassis 102 expands the EFD 100 into the expanded state. In another embodiment, the chassis 102 at least partially radially expands the EFD 100 as the EFD 100 exits the sheath 152 of the deployment catheter 150.

The upstream portion 106 expands to contact the interior wall of the aorta 12 at a location upstream from the brachiocephalic artery 16, seals against the aorta 12, and anchors the EFD 100 in position. The midsection 110 extends along the aortic arch 13, bending to follow the form thereof, and terminates at a point downstream from the subclavian artery 20. The downstream portion 108 expands to contact the interior surface of the aorta 12 downstream of the subclavian artery 20 to aid in retaining position of the EFD 100 along the aorta 12 and to maintain the passageway through the EFD 100 in a generally centrally located cross-sectional position within the aorta 12.

The filtration membrane 104 has sufficient flexibility and resilience to allow the chassis 102 to expand without substantial resistance. However, the filtration membrane 104 can be configured to limit the extent to which the chassis 102 can expand and/or to shape the form of the expanded chassis 102. Conversely, the membrane 104 can also be employed to increase the bias of the chassis 102 toward expansion and/or the membrane 104 can be eliminated along portions of the chassis 102, such as in the downstream portion 108 to increase the ability of the chassis 102 to expand (as depicted in FIGS. 2 and 4).

The spring memory and flexibility of the chassis 102 enables conformance of the EFD 100 to a wide variety of aortic formations/malformations. Perforation of the filtration membrane 104 over its entire area, including up to the upstream edge 112 of the EFD 100, aids to minimize the risk of occluding the coronary artery branches 16, 18, 20 within the ascending aorta 12. For example, during the initial moments of deployment and expansion of the EFD 100 as the sheath 202 of the deployment catheter 150 is pulled back, the upstream portion 106 expands to the interior surface of the aorta 12 before the midsection 110 is unsheathed. Perforation of the upstream portion 106 enables continued blood flow therethrough while the midsection 110 is being deployed. Prior EFD devices, like the EFD 10, did not include perforations in the upstream portion and thus risked momentarily impeding blood flow. Additionally, the perforations in the upstream portion 106 reduce the pressure drop across the upstream portion 106 as it is expanded which may reduce a risk of the upstream portion 106 being inverted back onto the exterior of the deployment catheter 150 as the EFD 100 is deployed.

Following full withdrawal of the chassis 102 from the sheath 152 of the deployment catheter 150, the retrieval component 130 is released from the carriage 160 and allowed to dangle in the downstream flow through the aorta 12. The deployment catheter 150 is withdrawn from the patient along the guidewire 158 and the desired surgical procedures, such as a TAVR procedure are completed. During the procedures, implements, implants, and other devices may be extended through the central bore of the EFD 100, such as by sliding along the guidewire 158. Emboli that are generated during such procedures and that are generally larger in size than the pore size of the filtration membrane 104 are transmitted through the EFD 100, bypassing the cranial arteries 16, 18, 20. The emboli are thus passed down the descending aorta 14 where they can be handled by the patient's body in a less detrimental manner than if they were allowed to flow into the cranial arteries 16, 18, 20 where they may result in a stroke or other, more severe harm.

Upon completion of the procedure(s) the EFD 100 may be left in place for a period of time to continue to protect the patient from emboli for a period of time or may be removed immediately. The EFD retrieval device 200 is employed to retrieve and remove the EFD 100 from the patient's body. The retrieval device 200 includes a catheter comprised of the sheath 202 and the core 204. The guidewire 158 is inserted through an axial passage in the core 204 to guide insertion of the retrieval device 200 into the patient's femoral artery and to the location of the EFD 100 by known procedures. The catheter is moved into position manually by the surgeon pushing or sliding the device 200 along the guidewire 158. Once in position for retrieval, the sheath 202 and core 204 are moveable relative to one another using the thumb tab 216 and slider 208 disposed in the handle 206 of the retrieval device 200.

The core 204 at the distal end of the retrieval catheter 200 includes a capture apparatus with a magnetic component. The capture apparatus may be deployed and actuated by slidably moving the slider 208 within the handle 206 in a first direction. The slider 208 may then be slid in an opposite second direction to engage and/or couple with the retrieval component 130. In one embodiment, the capture apparatus includes a plurality of fingers that are extended from the distal end of the sheath 202 such as by retracting the sheath 202. The fingers expand radially outward to open a space therebetween in which the magnetic component is positioned. The magnetic component magnetically attracts the retrieval component 130 thereby drawing it into the space between the fingers and forming a magnetic coupling therewith. The attractive force between the magnetic component and the retrieval component 130 is preferably sufficient to draw the two components together from a distance at least as large as the diameter of the aorta 12. Upon forming the magnetic coupling, the core 204 is retracted into the sheath 202 (or the sheath 202 is advanced over the fingers) by moving the slider 208 in an opposite second direction which causes the fingers to be contracted radially inward onto the retrieval component 130 and to trap the retrieval component 130 therebetween.

Following capture and engagement of the core 204 with the retrieval component 130, the surgeon may continue movement of the slider 208 in the second direction which simultaneously advances the sheath 202 upstream a distance $d_s$, while retracting the core 204 downstream a distance $d_c$; distances $d_s$ and $d_c$ being proportional based on the ratio r, as described above. As such, the core 204 is retracted at a rate relative to the advancement of the sheath 202 that compensates for the elongation of the EFD 100 as the EFD 100 collapses. The retrieval catheter 132 otherwise need not be moved by the surgeon. The EFD 100 can thereby be collapsed and retracted into the sheath 202 without movement or dragging thereof along the interior surfaces of the aorta 12.

The collapse of the EFD 100 is achieved through retraction of the core 204 which applies a tension force on the tail 126 causing the drawstring 124 to contract the fingers 118 of the downstream portion 108 radially inward and together. Such contraction is transmitted through the chassis 102 via the braided structure thereof causing further contraction along its length. Continued retraction of the core 204 and advancement of the sheath 202 advances the sheath 202 over the EFD 100 thus bringing the EFD into the interior of the sheath 202 and further collapsing the EFD 100. Upon full collapse and retraction of the EFD 100 into the sheath 202, the catheter may be withdrawn from the patient in a known manner.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. An embolic filtration device comprising:
   a chassis having a tubular form that is moveable between an expanded state and a collapsed state, in the expanded state the chassis having an upstream portion, a midsection, and a downstream portion, the upstream portion and the downstream portion each having a radial dimension greater than a radial dimension of the midsection, wherein in the expanded state the upstream portion and the downstream portion are configured to contact an interior wall of a human aorta, and in the collapsed state being disposable within a sheath of a catheter; and
   a filtration membrane disposed on the chassis to extend about a full circumference of the chassis and longitudinally from an upstream edge of the upstream portion and along the midsection at least to a point that is adjacent a downstream terminus of the midsection, the membrane being perforated to enable blood to pass therethrough but preventing passage of hazardous emboli through the membrane, and wherein the downstream portion of the chassis does not include the filtration membrane.

2. The embolic filtration device of claim 1, wherein the upstream edge of the chassis includes a plurality of projections spaced around the circumference of the chassis and extending generally axially in an upstream direction and wherein an upstream edge of the filtration membrane follows the upstream edge of the chassis.

3. The embolic filtration device of claim 1, further comprising:
   a plurality of fingers spaced about a circumference of a downstream end of the downstream portion and extending axially in a downstream direction, each finger including an eyelet disposed at a distal end the finger;
   a drawstring extending through the plurality of eyelets and including a tail extending in the downstream direction.

4. The embolic filtration device of claim 3, wherein the eyelets maintain the drawstring adjacent to the distal ends of the fingers.

5. The embolic filtration device of claim 3, wherein a tension force applied to the tail draws the plurality of fingers radially inward and collapses the chassis to the collapsed state.

6. The embolic filtration device of claim 3, wherein a longitudinal length of the chassis increases a distance $\Delta l$ from a length $l_o$ to a length $l_f$ as the chassis collapses from the expanded state to the collapsed state and further comprising:
   a retrieval device having a sheath, a core, and an actuation apparatus configured to simultaneously advance the sheath and retract the core, wherein a ratio of the core retraction relative to the sheath advancement is $$r = \frac{\Delta l}{l_f}.$$

7. The embolic filtration device of claim 3, further comprising:
   a retrieval component coupled to a downstream end of the tail, the retrieval component being engageable by a retrieval catheter to aid removal of the embolic filtration device from a patient's aorta.

8. The embolic filtration device of claim 7, wherein the retrieval component further comprises:
   a first magnet having an axial bore and a pair of diametrically aligned slots in a top surface thereof;
   a second magnet having an axial bore aligned with and stacked on the first magnet, the tail extending through the axial bores of the first and second magnets and including a bifurcated portion forming two free ends that extend along a bottom surface of the first magnet, around sides of first magnet, into the slots, and back through the axial bore of the second magnet, the two free ends of the bifurcated portion being secured to the tail.

9. The embolic filtration device of claim 8, wherein the retrieval component is coated with a biocompatible material.

10. The embolic filtration device of claim 1, wherein the perforation of the membrane provides a plurality of pores having a diametrical dimension less than or equal to 100 µm.

11. An embolic filtration system comprising:
    a chassis having a tubular form that is moveable between an expanded state and a collapsed state, in the expanded state the chassis having an upstream portion, a midsection, and a downstream portion, the upstream portion and the downstream portion each configured to bias to expand into contact with an interior wall of a human aorta, the midsection having a radial dimension in the expanded state that is less than a radial dimension of the human aorta, and in the collapsed state being disposable within a sheath of a catheter;
    a plurality of fingers spaced about a circumference of a downstream end of the downstream portion and extending axially in a downstream direction, each finger including an eyelet disposed at a distal end the respective finger;
    a drawstring extending through the plurality of eyelets and including a tail extending in the downstream directions;
    a retrieval component coupled to a downstream end of the tail, the retrieval component being engageable by a retrieval catheter to aid removal of the embolic filtration device from a patient's aorta, the retrieval component including a first magnet having an axial bore and a pair of diametrically aligned slots in a top surface thereof and a second magnet having an axial bore aligned with and stacked on the first magnet, the tail extending through the axial bores of the first and second magnets and including a bifurcated portion forming two free ends that extend along a bottom surface of the first magnet, around sides of first magnet, into the slots, and back through the axial bore of the second magnet, the two free ends of the bifurcated portion being secured to the tail; and a filtration membrane disposed on the chassis to extend about a full circumference of the chassis and longitudinally from an upstream edge of the upstream portion at least to a downstream terminus of the midsection, at least a portion of the membrane disposed on the midsection being perforated to enable blood to pass therethrough but preventing passage of hazardous emboli through the membrane.

12. The embolic filtration device of claim 11, wherein the upstream edge of the chassis includes a plurality of projections spaced around the circumference of the chassis and extending generally axially in an upstream direction and wherein an upstream edge of the filtration membrane follows the upstream edge of the chassis.

13. The embolic filtration device of claim 11, wherein the downstream termination of the filtration membrane is positioned at or just downstream of a contact point between the downstream portion and an interior surface of the aorta.

14. The embolic filtration device of claim 11, wherein the eyelets maintain the drawstring adjacent to the distal ends of the fingers.

15. The embolic filtration device of claim 11, wherein a tension force applied to the tail draws the plurality of fingers radially inward and collapses the chassis to the collapsed state, wherein a longitudinal length of the chassis increases a distance $\Delta l$ from a length $l_o$ to a length $l_f$ as the chassis collapses from the expanded state to the collapsed state, and wherein the embolic filtration device further comprises:

a retrieval device having a sheath, a core, and an actuation apparatus configured to simultaneously advance the sheath and retract the core, wherein a ratio of the core retraction relative to the sheath advancement is $$r = \frac{\Delta l}{l_f}.$$

* * * * *